(12) United States Patent
Venter et al.

(10) Patent No.: US 6,506,930 B1
(45) Date of Patent: Jan. 14, 2003

(54) PROCESS FOR PREPARING ALKYL (METH)ACRYLATES

(75) Inventors: Jeremia Jesaja Venter, Warrington; Mario Giuseppe Luciano Mirabelli, Horsham, both of PA (US)

(73) Assignee: Rohm and Haas Company, Philadelphia, PA (US)

(*) Notice: Subject to any disclaimer, the term of this patent is extended or adjusted under 35 U.S.C. 154(b) by 0 days.

(21) Appl. No.: 09/417,400

(22) Filed: Oct. 13, 1999

Related U.S. Application Data

(63) Continuation-in-part of application No. 09/192,675, filed on Nov. 16, 1998, now abandoned.
(60) Provisional application No. 60/066,939, filed on Nov. 17, 1997.

(51) Int. Cl.[7] .................................. C07C 69/54
(52) U.S. Cl. ........................ 560/205; 560/218
(58) Field of Search ................ 560/205, 217, 560/225, 261, 265, 218

(56) References Cited

U.S. PATENT DOCUMENTS

| | | | | |
|---|---|---|---|---|
| 5,322,960 A | * | 6/1994 | Sakamoto et al. | |
| 5,504,243 A | * | 4/1996 | Sakamoto et al. | |
| 5,510,514 A | * | 4/1996 | Fauconet | |
| 5,734,074 A | * | 3/1998 | Dockner et al. | |

FOREIGN PATENT DOCUMENTS

| WO | 9907664 | * | 7/1998 |
|---|---|---|---|

* cited by examiner

Primary Examiner—Paul J. Killos
Assistant Examiner—Robert W. Deemie
(74) Attorney, Agent, or Firm—Alan Holler

(57) ABSTRACT

A process for preparing alkyl acrylates is disclosed. The process provides for the synthesis of alkyl (meth)acrylates, hydrolysis of process impurities into starting materials and separation of starting materials and reaction products in one reactor.

11 Claims, 1 Drawing Sheet

PROCESS FOR PREPARING ALKYL (METH)ACRYLATES

Figure 1:
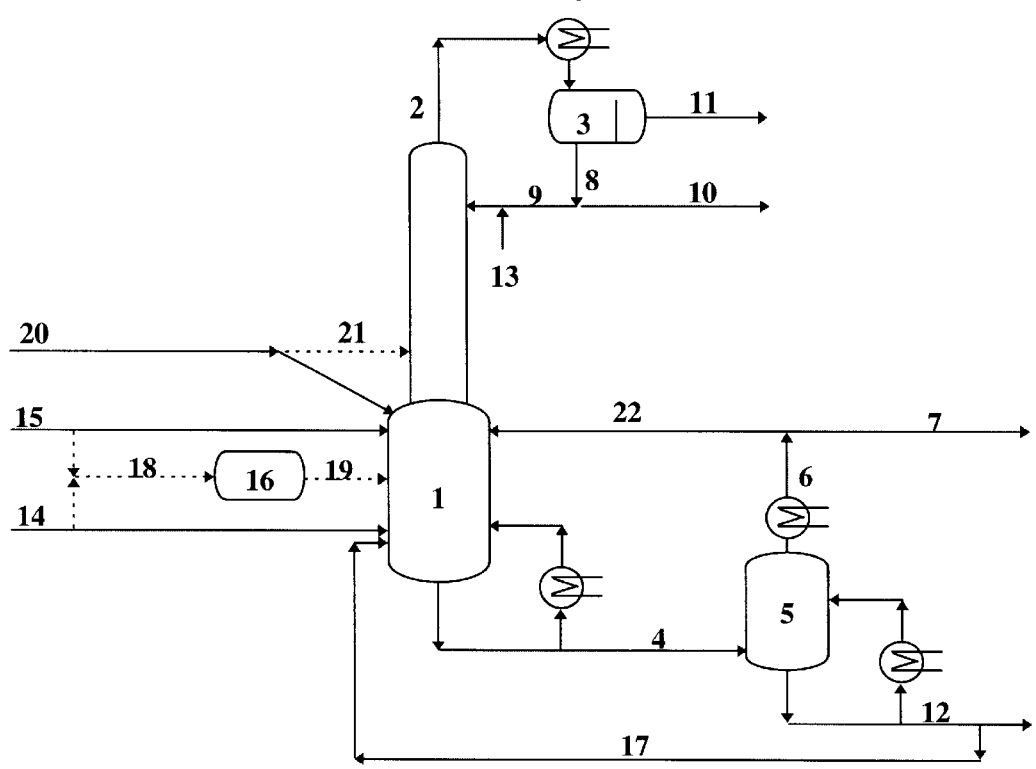

This application is a continuation-in-part of 09/192,675 filed Nov. 16, 1998 which claim benefit of provisional application 60/066,931 filed Nov. 17, 1997.

Co-pending U.S. patent application Ser. No. 08/797,380 discloses a process for preparing BA in which process impurities are hydrolyzed in separate reactors. In addition, the AA/BA separation is performed in a separate low pressure distillation column. Although the patent application addresses the issue of conversion of impurities to starting materials, it does not provide a BA process in which BA is prepared in a high water reaction medium which allows (1) operation under atmospheric pressure, (2) separation of AA/BA in the reactor, and (3) recovery of starting materials from process impurities in one unit.

This invention relates to a process for preparing alkyl (meth)acrylates. Specifically, the process provides for the synthesis of alkyl (meth)acrylates, the hydrolysis of process impurities into starting materials, and the separation of reaction products and starting materials in one reactor.

Alkyl (meth)acrylates are important monomers in commercial polymerization processes. Conventionally, alkyl (meth)acrylates, such as butyl acrylate ("BA"), are commercially prepared by a direct esterification process. Typically, butanol ("BuOH") and acrylic acid ("AA") are reacted in the presence of an acid catalyst thereby yielding butyl acrylate and water. The direct esterification is generally run at elevated temperature and reduced pressure. During the reaction, impurities are formed such as dibutyl ether ("DBE"), butyl-β-butoxy propionate ("BBBP"), butyl-β-hydroxy propionate ("BBHP"), butyl-acryloxypropionate ("BAOPA"), and acryloxypropionic acid ("AOPA"). These impurities, if not converted back to starting materials, result in lower yield.

Such impurities are usually removed from the reactor and treated to produce starting materials which can be reused. As a result, these processes are less efficient and require additional capital investment costs for separate reactors. Furthermore, conventional BA preparation processes operate at reduced pressure, necessitating a need for larger sized equipment. Consequently, there is a need for a more efficient, lower cost butyl acrylate process which converts process impurities back to starting materials, does so in the same reactor in which BA is produced and which can be operated at atmospheric pressure.

The present invention discloses a process of preparing alkyl (meth)acrylates which converts process impurities back to starting materials and further reacts them in one reactor. The addition of water during the direct esterification reaction also provides an alkyl (meth)acrylate preparation process which does not require reduced pressure and facilitates the recovery of starting materials from process impurities. Furthermore, separation of the reaction product, such as BA, and the starting (meth)acrylic acid, such as AA, can also be effected in the reactor. Consequently, the present invention provides a process which is more efficient and economical than conventional alkyl (meth)acrylate preparation processes known in the art.

One aspect of the present invention provides a process which includes: (A) charging a reactor with a $C_1$–$C_4$ alcohol, a (meth)acrylic acid, a strong acid catalyst, and at least 5% by weight water to form a reaction mixture; (B) reacting the reaction mixture to form a $C_1$–$C_4$ alkyl (meth)acrylate and process impurities, wherein the process impurities formed are hydrolyzed in the reactor; and (C) separating the $C_1$–$C_4$ alkyl (meth)acrylate and water formed during the reaction from the reaction mixture.

Another aspect of the present invention provides a process which includes: (A) charging a reactor with butanol, acrylic acid, a strong acid catalyst, and at least 5% by weight water to form a reaction mixture; (B) reacting the reaction mixture to form butyl acrylate and process impurities, wherein the process impurities are hydrolyzed in the reactor; and (C) separating the butyl acrylate and water formed during the reaction from the reaction mixture.

A further aspect of the present invention provides a process which includes: (A) charging a reactor with butanol, acrylic acid, 3.5 to 15% by weight sulfuric acid, 6 to 18% by weight water and at least one inhibitor to form a reaction mixture, wherein the butanol and acrylic acid are charged to the reactor in an acrylic acid to butanol molar ratio of 1:1 to 1:1.7; (B) reacting the reaction mixture to form butyl acrylate and process impurities, wherein the process impurities are hydrolyzed in the reactor; and (C) separating the butyl acrylate and water formed during the reaction from the reaction mixture by azeotropic distillation.

Another further aspect of the present invention provides a reaction mixture, including: acrylic acid, butanol, from 3.5 to 15% by weight sulfuric acid, from 6 to 18% by weight water and from 0.001 to 1.0% by weight 4-hydroxy-2,2,6, 6-tetramethyl-1-piperidinyloxy.

As used herein, the term "(meth)acrylic" acid is meant to include both acrylic acid and methacrylic acid. In a like manner, the term "(meth)acrylate" is meant to include both acrylate and methacrylate.

As used herein, BuOH refers to n-butanol, i.e., 1-butanol and the term "butanol" includes within its scope all butanol isomers as well as mixtures thereof.

The term "alkyl" is meant to include branched chain, straight chain or cyclic alkyl groups. As used herein the terminology "($C_1$–$C_4$)" or "($C_1$–$C_{10}$)" means a group having from 1 to 4 or 1 to 10 carbon atoms per group.

As used herein, the terms "AA rich" or "BA rich" are understood to mean fractions or components where AA or BA is the major (greater than 50% by weight) organic component of the composition.

Throughout this specification and claims, unless otherwise indicated, references to percentages are by weight, all temperatures by degree centigrade and all pressures are atmospheric.

FIG. 1 illustrates the equipment and the flow lines utilized in one embodiment of the process of the present invention, including the direct esterification/hydrolysis reactor 1 which is a stirred reactor having a distillation column on top of it; line 2, which carries a vaporized distillate mixture, which includes BA, from 1 to a phase separator 3, the phase separator 3 separates the vaporized distillate into a BA rich organic phase and an aqueous distillate phase; line 11, which carries the BA rich organic distillate separated in 3 forward to a separation section; line 8 which carries the aqueous distillate separated in 3 to line 9 to be recycled to 1, and to line 10 to carry it forward to be treated, generally to recover material from aqueous waste; line 4, which carries the AA rich bottoms from 1 to bleed stripper 5, which is the cracking reactor; line 6, which carries the distillate, including recovered BuOH and AA from 5 to be recycled to 1 through line 22, and to line 7 which carries the distillate from 5 forward to be treated, generally as waste; line 12, which carries the bottoms from 5 forward to be treated, generally as waste and optionally to line 17, which recycles bottoms from 5 to 1; line 13, which may feed inhibitor to the reactor; line 14, which feeds catalyst to the reactor; line 15, which feeds fresh AA and BuOH to the reactor; an optional plug flow reactor 16; an optional line 18 for feeding AA, BuOH, and catalyst to 16; an optional line 19 for taking the material from 16 to 1; line 20, which carries the BuOH, BA, and AA recovered in the separation section from lines 10 and 11 back to the reactor 1; and optional line 21 which returns recovered material to an alternative feed location in reactor 1.

As recited above, in step (A) of the present invention $C_1$–$C_4$ alcohol, a (meth)acrylic acid, a strong acid catalyst, and water are charged to a reactor to form a reaction mixture.

Generally, the $C_1$–$C_4$ alcohol is a branched or straight chain alkanol having 1 to 4 carbon atoms or mixture thereof. Specific examples include, but are not limited to, methanol, ethanol, n-propanol, isopropanol, n-butanol, 2-butanol, tert-butanol or mixtures thereof. Furthermore, it is contemplated that the $C_1$–$C_4$ alcohol may be substituted, for example, with halogen, hydroxide, alkoxide, cyano, nitro, etc. In one embodiment, the alcohol is butanol. In a preferred embodiment, the alcohol is n-butanol.

Also present in the reaction mixture is (meth)acrylic acid or substituted meth(acrylic) acid substituted with, for example, with halogen, hydroxide, alkoxide, cyano, nitro, etc. In one embodiment, acrylic acid or methacrylic acid or a mixture thereof is present. In a preferred embodiment, the unsaturated acid is acrylic acid. The (meth)acrylic acid and alcohol are present in a molar ratio of 1:1 to 1:1.7, preferably 1:1.1 to 1:1.6, more preferably 1:1.25 to 1:1.45. It is also contemplated that other unsaturated acids such as crotonic acid, cinnamic acid, maleic acid, fumaric acid, etc., which can participate in a transesterification reaction with an alcohol may be utilized in the process of the present invention.

A strong acid catalyst is also present in the reaction mixture. Suitable examples of such an acid catalyst include, but are not limited to, sulfuric acid, methane sulfonic acid, benzene sulfonic acid, p-toluene sulfonic acid, mixtures thereof, or a polymer supported alkyl sulfonic acids such as AMBERLYST™ 15 resin or NAFION-H™ resin. Generally, the alkyl sulfonic acid is a $C_1$ to $C_{10}$ alkyl sulfonic acid. In one embodiment, the strong acid catalyst is a a sulfur containing acid or sulfur containing polymer supported acid. In a preferred embodiment, the strong acid catalyst is sulfuric acid. The concentration of strong acid catalyst by total weight of the reaction mixture in the direct esterification/hydrolysis reactor is typically 3.5 to 15% by weight, preferably 3 to 12% by weight, and more preferably 5 to 8% by weight.

Water is also present in the reaction mixture provided in step (A). Generally, any water, such as tap water, distilled water or deionized water, suitable for use in a direct trans-esterification reaction, may be used. Furthermore, at least some of the water provided may be recycled water of reaction which has been removed during separation of the reaction product from the starting materials. The addition of water provides a water reaction medium in the reactor which enables operation under atmospheric conditions and the hydrolysis of reaction byproducts to recover starting materials as well as separation of reaction products from starting materials in one reactor.

At least one inhibitor may also be charged to the reactor in step (A). Typically, from 0.001 to 1.0%, preferably 0.001 to 0.5%, and more preferably 0.001 to 0.1% by total weight of reaction mixture of at least one inhibitor, if used, is present during the direct esterification process to prevent polymerization. Suitable inhibitors include hydroquinone, the mono-methyl ether of hydroquinone, 2,2,6,6-tetramethyl-1-piperidinyloxy (TEMPO), 4-hydroxy 2,2,6,6-tetramethyl-1-piperidinyloxy (4HTEMPO), butylated hydroxy anisole, naphthoquinone, anthranil, and combinations thereof. Derivatives of these inhibitors may also be used. Such derivatives include, but are not limited to, 4-methacryloyloxy-2,2,6,6-tetramethyl piperidinyl free radical and 4-hydroxy-2,2,6,6-tetramethyl N-hydroxy piperidine. In a preferred embodiment, the at least one inhibitor is 4-hydroxy-2,2,6,6-tetramethyl-1-piperidinyloxy. In another embodiment, the at least one inhibitor is 2,2,6,6-tetramethyl-1-piperidinyloxy. In another embodiment, 4-hydroxy-2,2,6,6-tetramethyl-1-piperidinyloxy and another inhibitor such as, the methyl ether of hydroquinone are used.

In one embodiment, the alcohol is butanol, the (meth) acrylic acid is acrylic acid, the acid catalyst is sulfuric acid and the inhibitor is 4-hydroxy-2,2,6,6-tetramethyl-1-piperidinyloxy. In a further embodiment the water is present at from 6 to 18% by total weight of reaction mixture and strong acid catalyst is present at 3.5 to 15% by total weight of reaction mixture.

As recited above, the present invention utilizes one reactor wherein direct esterification of AA and BuOH; hydrolysis of reaction byproducts including BBBP, BBHP, and BAOPA; and separation of BA and AA are achieved. Generally, any reactor suitable or adaptable for a process wherein a direct esterification reaction, hydrolysis of reaction byproducts formed during the transesterification reaction, and separation of reaction products from starting materials occurs in the reactor may be used. In one embodiment, the reactor may be a stirred tank equipped with a distillation column. In a preferred embodiment, the distillation column may be situated directly on top of the reactor (as in FIG. 1) and may be a fractional distillation column. Generally, the distillation column contains from 20 to 100 trays. It is preferred that the column contains from 20 to 70 trays. It is more preferred that the column contains from 40 to 50 trays. The column has means for feeding AA, BuOH, a strong acid catalyst, water, and at least one inhibitor. The reactor also has means for removing the bottoms.

In step (B) the reaction mixture is reacted to form a $C_1$–$C_4$ alkyl (meth)acrylate and reaction byproducts, while reaction byproducts formed during the reaction are hydrolyzed in the same reactor.

The direct esterification reaction may be run by feeding AA and BuOH through lines 15, 20, and 22 to the direct esterification/hydrolysis reactor 1 in an AA to BuOH molar ratio ranging from 1:1 to 1:1.7, preferably 1:1.25 to 1:1.45. The AA and BuOH may also be fed along with sulfuric acid to a plug flow reactor 16, and then to the direct esterification/hydrolysis reactor 1. Inhibitor, if used, is fed into the reactor using line 13. The AA, BuOH, inhibitor, strong acid catalyst, and water form a reaction mixture in the direct esterification/hydrolysis reactor. The AA and BuOH are reacted to a conversion on AA of from 50 to 95%, preferably 60 to 95%, more preferably 70 to 95%.

During the direct esterification reaction, the reactor must have at least 5% by total weight of reaction mixture of water for efficient hydrolysis operation. Preferably, the reactor has from 6 to 18% by weight water during the direct esterification reaction. More preferably, the reactor has from 8 to 12% by weight water during the direct esterification reaction. Water content may be maintained by returning the condensed and separated aqueous distillate from the reactor through line 9 back to the reactor. Water may also be added through any of the feed lines as is necessary. The water in the reactor hydrolyzes reaction byproducts formed during the reaction. Specific examples of hydrolysis reactions which occur include, but are not limited to, reactions where BBBP is hydrolyzed to 2 BuOH and 1 AA, BBHP is hydrolyzed to 1 BuOH and 1 AA, and BAOPA is hydrolyzed to 1 BuOH and 2 AA.

The direct esterification reaction and hydrolysis are run at a temperature of from 100° C. to 140° C., preferably 105° C. to 135° C., and more preferably 115° C. to 130° C. The direct esterification reaction and hydrolysis are run at pressures from 100 mm Hg to 760 mm Hg. Atmospheric pressure is preferred. The residence time in the direct esterification/hydrolysis reactor is typically from 0.5 to 5 hours, preferably from 1 to 4 hours, and more preferably from 2 to 3 hours.

In step (C), the $C_1$–$C_4$ alkyl (meth)acrylate and water formed during the reaction of the alcohol with the (meth) acrylic acid are separated from the reaction mixture by methods known in the art such as distillation, phase separation, etc. In a preferred embodiment, the $C_1$–$C_4$ alkyl (meth)acrylate and water formed during the reaction are separated from the reaction mixture by azeotropic distillation. In a more preferred embodiment, the $C_1$–$C_4$ alkyl (meth)acrylate is azeotropically distilled with water (aqueous reflux) and BuOH under the conditions described above. Accordingly, the water added to the reaction medium as well as water produced from the transesterification reaction of AA and BuOH provide an aqueous medium which enhances separation of AA and BA in the reactor. The distillate may then be taken through line 2 to a phase separator 3. In the phase separator, an organic phase which is BA rich and contains BuOH, and an aqueous phase which contains water and AA separate. The organic phase may be taken through line 11 to a separation section, wherein pure BA is obtained. BuOH may be recovered from the separation section and recycled. Part of the aqueous phase is taken through line 8 to line 9 to be recycled to the reactor to maintain the appropriate amount of water in the reactor. The rest of the aqueous phase is taken through line 8 to line 10 to carry it forward to be recovered and treated, generally as waste.

The bottoms of the direct esterification reactor contain strong acid catalyst, BA, AA, BuOH, AOPA, BBPA, and BHPA. A bleed stripper 5 may be utilized to crack acryloxy proprionic acid ("AOPA"), the dimer of AA; beta-n-butoxy propionic acid ("BBPA"), and beta-hydroxy propionic acid ("BHPA"). Accordingly, the bottoms may be taken through line 4 to bleed stripper 5 (the cracking reactor), where AOPA is cracked to 2 AA; BBPA is cracked to 1 BuOH and 1 AA; and BHPA is cracked to 1 AA. The cracking reactor may be a continuous stirred tank reactor. Where the cracking reactor is incorporated in the process, the liquid in the cracking reactor is maintained at from 5 to 25% by weight strong acid, preferably sulfuric acid. The cracking reactor is operated at a temperature ranging from 90 to 140° C., preferably from 110 to 140° C. The cracking reactor is operated at a pressure ranging from 20 to 200 mm Hg, although higher pressures, up to 800 mm Hg may be used. The residence time in the cracking reactor is typically from 0.5 to 10 hours, preferably 0.5 to 6 hours, more preferably 0.5 to 3 hours.

Part of the BA, AA, BuOH and water generated in the cracking reactor may be taken overhead and recycled to the direct esterification/hydrolysis reactor through line 6 to line 22. The rest of the BA, AA, BuOH and water generated in the cracking reactor may be taken overhead through line 6 to line 7 to be carried forward to be treated, generally as waste. The bottoms of the cracking reactor may be taken through line 12 to be carried forward to be treated, generally as waste, or may be recycled to the direct esterification/hydrolysis reactor 1 through line 17.

| | |
|---|---|
| % = percent | ° C. = degrees Centigrade |
| BA = butyl acrylate | mm = millimeters |
| ml = milliliters | ml/min = milliliters per minute |
| AA = acrylic acid | BuOH = butanol |
| AOPA = acryloxypropionic acid | BBPA = beta-n-butoxy propionic acid |
| BHPA = beta-hydroxy propionic acid | BBBP = butyl-β-butoxy propionate |
| BBHP = butyl-β-hydroxy propionate | BAOPA = butyl-acryloxypropionate |
| cm = centimeters | Hg = Mercury |
| g/hr = grams per hour | |

The following examples illustrate the process of the present invention.

Materials: AA, BA, and BuOH were obtained from plant production streams. The inhibitors used are commercially available.

Analyses: Standard methods were used for determination of water, monomer, BuOH, and residual impurities. AOPA, BBBP, BBHP, and BAOPA levels were determined by gas/liquid chromatography using flame ionization detection. Sulfuric acid determinations were obtained using a pH probe and alcoholic tetrabutylammonium hydroxide titrant.

EXAMPLE 1

Preparation of Butyl Acrylate

A direct esterification/hydrolysis reactor was set up using a 5,000 ml round bottom flask connected to a multi-tube Hastalloy C-276 steam jacketed reboiler. A 45 tray, 5.08 cm Oldershaw fractional distillation column was situated directly on top of the glass reactor, and was considered to be part of the reactor. An overhead system of two standard glass, water cooled condensers connected in series was connected to the fractional distillation column. A 2,000 ml glass fraction cutter was connected to the second condenser. A bleed stripper (cracking reactor) was set up using a 500 ml flask equipped with an electric heating mantle, temperature controllers, a stirrer and a water cooled distillation head having a take-off port leading to a 125 ml fraction cutter. A peristaltic pump was provided for pumping the bottoms stream directly from the reboiler. A graduated cylinder equipped with a Teflon stopcock for easy sample removal was used for collecting the bottoms stream.

AA, BuOH, and sulfuric acid were fed to the direct esterification reactor. The direct esterification reactor was set to 128° C. and 760 mm Hg. The bleed stripper was set to 130° C. and 35 mm Hg with 26% by weight sulfuric acid present. The inhibitor pump was then turned on to pump a solution of 0.25% 4-hydroxy-2,2,6,6-tetramethyl-1-piperidinyloxy and 0.018% methyl ether of hydroquinone in BA. Once the top trays of the fractional distillation column were wetted with inhibitor solution, steam was introduced to the reboiler. When the reboiler reached the desired temperature and distillate was observed in the overhead system, the following were pumped into the reactor: 3.7 g/hr inhibitor via positive displacement FMI piston pump, 234.4 g/hr total AA (including recycle) via positive displacement FMI piston pump, 382.5 g/hr total BuOH (including recycle) via positive displacement FMI piston pump, and 4.5 g/hr sulfuric acid via a peristaltic pump utilizing appropriate tubing compatible with strong mineral acid. A portion of the water recovered from overhead was fed back to the reactor for a reflux feed rate of 461.8 g/hr. The residence time in the reactor was 180 minutes. Distillate and bottoms streams were collected hourly and analyzed for strong acid, AA, and water to determine when steady state had been achieved. Once steady state was achieved, all process streams were thoroughly analyzed.

Once distillate was observed in the bleed stripper water cooled distillation head, the feed pumps were turned on and distillate and bottoms streams were collected. To the bleed stripper was pumped 66.3 g/hr bottoms from the direct esterification reactor. The bottoms stream was collected via an overflow system in which the overflow point was set at a particular volume, which represented the desired residence time. Once steady state was achieved, the distillate stream was thoroughly analyzed. The residence time in the bleed stripper was 235 minutes. The distillate recovered overhead was pumped back to the direct esterification reactor at a rate of 47.1 g/hr. The process had a yield of 108% of BA based on AA. The process had a BA yield of 95% based on BuOH. Process yields in excess of 100% are possible because BA can be recovered from AOPA present in the AA feed.

EXAMPLE 2
Preparation of Butyl Acrylate with Plug Flow Reactor Utilization

In this example, a plug flow reactor was inserted before the direct esterification reactor. The rest of the equipment and procedures were the same as in Example 1. The direct esterification reactor was set to 115° C. and 760 mm Hg. To the plug flow reactor was pumped: 219 g/hr AA, 201.3 g/hr BuOH, and 2.2 g/hr sulfuric acid. To the direct esterification reactor was pumped 3.6 g/hr inhibitor, 422.5 g/hr effluent from the plug flow reactor, and 2 g/hr sulfuric acid. A portion of the water recovered from overhead was pumped back to the reactor for a reflux rate of 477.7 g/hr. The residence time in the reactor was 180 minutes. The bleed stripper was operated at 130° C. and 35 mm Hg with 17.5% by weight sulfuric acid present. To the bleed stripper was pumped 96.8 g/hr bottoms from the direct esterification reactor. The residence time in the bleed stripper was 195 minutes. The distillate recovered overhead was pumped back to the direct esterification reactor at a rate of 72.1 g/hr. The process had a BA yield of 98% based on AA. The process had a BA yield of 100% based on BuOH.

EXAMPLE 3
Preparation of Butyl Acrylate with Cracking Reactor Bottoms Recycle In this example, the bottoms from the cracking reactor were recycled to the direct esterification reactor. The rest of the equipment and procedures were the same as in Example 1. The direct esterification reactor was set to 130° C. and 760 mm Hg. To the direct esterification reactor was pumped 3.8 g/hr inhibitor, 230.8 g/hr AA, 377.4 g/hr BuOH, and 3.2 g/hr sulfuric acid. A portion of the water recovered from overhead was pumped back to the reactor for a reflux rate of 468.7 g/hr. The residence time in the reactor was 154 minutes. The bleed stripper was operated at 130° C. and 35 mm Hg with 22.2% by weight sulfuric acid present. To the bleed stripper was pumped 65 g/hr bottoms from the direct esterification reactor. The residence time in the bleed stripper was 195 minutes. The distillate recovered overhead was pumped back to the direct esterification reactor at a rate of 36.4 g/hr. The bottoms of the bleed stripper were recycled to the direct esterification reactor at a rate of 10.5 g/hr. The process had a BA yield of 98% based on AA. The process had a BA yield of 100% based on BuOH.

EXAMPLE 4
Preparation of Butyl Acrylate Using Methane Sulfonic Acid Catalyst In this example, methane sulfonic acid was substituted for sulfuric acid as the catalyst. The rest of the equipment and procedures were the same as in Example 1. The direct esterification reactor was set to 119° C. and 760 mm Hg. To the direct esterification reactor was pumped 3.8 g/hr inhibitor, 212.1 g/hr AA, 383.9 g/hr BuOH, and 5.2 g/hr methane sulfonic acid. A portion of the water recovered from overhead was pumped back to the reactor for a reflux rate of 470.5 g/hr. The residence time in the reactor was 131 minutes. The bleed stripper was operated at 130° C. and 35 mm Hg with 28% by weight methane sulfonic acid present. To the bleed stripper was pumped 73 g/hr bottoms from the direct esterification reactor. The residence time in the bleed stripper was 278 minutes. The distillate recovered overhead was pumped back to the direct esterification reactor at a rate of 57.3 g/hr. The process had a BA yield of 98% based on AA. The process had a BA yield of 100% based on BuOH.

The above examples demonstrate that the process of this invention is effective at producing alkyl (meth)acrylates in high yields by direct esterification efficiently and economically. That is, the process is run in a high aqueous medium wherein:

(1) reaction pressures can be atmospheric and need not be reduced pressures;

(2) AA and BA, i.e. starting materials and reaction product are separated in the reactor; and (3) the transesterification reaction and byproduct hydrolysis reaction occur in the same reactor.

Accordingly, the need for additional and separate equipment and process steps (for byproduct hydrolysis and/or reaction product/starting material separation) and/or larger equipment (because of lower reaction pressures) is eliminated.

What is claimed is:

1. A process comprising:

(A) charging a reactor with a $C_1$–$C_4$ alcohol; a (meth)acrylic acid; a strong acid catalyst selected from the group consisting of sulfuric acid, alkyl sulfonic acid and polymer supported alkyl sulfonic acid; at least one inhibitor selected from the group consisting of 2,2,6,6-tetramethyl-1-piperidinyloxy, 4-hydroxy-2,2,6,6-tetramethyl-1-piperidinyloxy, 4-methacryloyloxy-2,2,6,6-tetramethyl piperidinyl free radical and 4-hydroxy-2,2,6,6-tetramethyl N-hydroxy piperidine; and at least 5% by weight water to form a reaction mixture;

(B) reacting the reaction mixture to form a $C_1$–$C_4$ alkyl (meth)acrylate and process impurities, wherein the process impurities are hydrolyzed in said reactor; and (C) separating the $C_1$–$C_4$ alkyl (meth)acrylate and water formed during the reaction from the reaction mixture.

2. The process according to claim 1 wherein the strong acid catalyst is sulfuric acid.

3. The process according to claim 1 wherein the inhibitor is 4-hydroxy-2,2,6,6-tetramethyl-1-piperidinyloxy.

4. The process according to claim 1, further comprising charging said reactor with a second inhibitor selected from the group consisting of hydroquinone, the mono-methyl ether of hydroquinone, butylated hydroxy anisole, naphthoquinone, anthranil and combinations thereof.

5. The process according to claim 1 wherein the separation of the $C_1$–$C_4$ alkyl (meth)acrylate and water from the reaction mixture is achieved by azeotropic distillation directly from the reaction mixture.

6. The process according to claim 5 wherein the azeotropic distillation is carried out in the reactor using aqueous reflux in a distillation column having from 20 to 100 trays.

7. The process according to claim 6 wherein the azeotropic distillation is carried out at atmospheric pressure.

8. The process according to claim 1 wherein the $C_1$–$C_4$ alcohol is butanol and the (meth)acrylic acid is acrylic acid.

9. The process according to claim 8 wherein the butanol and the acrylic acid are charged to the reactor in an acrylic acid to butanol molar ratio of 1:1 to 1:1.7.

10. The process according to claim 1 wherein the water is present at from 6 to 18% by weight and the strong acid catalyst is present at from 3.5 to 15% by weight.

11. A reaction mixture, comprising:
acrylic acid, butanol, from 3.5 to 15% by weight sulfuric acid, from 6 to 18% by weight water and from 0.001 to 1.0% by weight 4-hydroxy-2,2,6,6-tetramethyl-1-piperidinyloxy.

* * * * *